United States Patent
Sakamoto et al.

(10) Patent No.: US 9,889,319 B2
(45) Date of Patent: Feb. 13, 2018

(54) PARTICLE BEAM IRRADIATION APPARATUS

(71) Applicant: MITSUBISHI ELECTRIC CORPORATION, Chiyoda-ku, Tokyo (JP)

(72) Inventors: Yusuke Sakamoto, Tokyo (JP); Yuehu Pu, Tokyo (JP); Hisashi Harada, Tokyo (JP); Taizo Honda, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/116,352

(22) PCT Filed: Apr. 10, 2014

(86) PCT No.: PCT/JP2014/060395
§ 371 (c)(1),
(2) Date: Aug. 3, 2016

(87) PCT Pub. No.: WO2015/155868
PCT Pub. Date: Oct. 15, 2015

(65) Prior Publication Data
US 2017/0021197 A1    Jan. 26, 2017

(51) Int. Cl.
*A61N 5/00* (2006.01)
*A61N 5/10* (2006.01)

(52) U.S. Cl.
CPC ............ *A61N 5/1071* (2013.01); *A61N 5/10* (2013.01); *A61N 5/1044* (2013.01);
(Continued)

(58) Field of Classification Search
CPC ....... A61N 5/1071; A61N 5/1077; A61N 5/10
(Continued)

(56) References Cited

U.S. PATENT DOCUMENTS

2004/0227104 A1    11/2004    Matsuda et al.
2006/0022153 A1    2/2006    Matsuda et al.
(Continued)

FOREIGN PATENT DOCUMENTS

EP    1 656 966 A1    5/2006
JP    3737098 B2    1/2006
(Continued)

OTHER PUBLICATIONS

International Search Report (PCT/ISA/210) dated May 20, 2014, by the Japanese Patent Office as the International Searching Authority for International Application No. PCT/JP2014/060395.
(Continued)

*Primary Examiner* — Michael Maskell
(74) *Attorney, Agent, or Firm* — Buchanan Ingersoll & Rooney PC

(57) ABSTRACT

A particle beam irradiation apparatus radiates a particle beam plural times per one irradiation position. A storage unit stores a dose to be radiated each of the times (divisional target dose). A dose monitor measures the dose of the particle beam radiated to the irradiation position. At the first time of radiation, a controller outputs an interruption signal when the dose measured by the dose monitor reaches the divisional target dose. The dose monitor measures a dose (excessive dose) radiated after the interruption signal is outputted until the particle beam is actually interrupted. Then, it is defined: Corrected Dose value=Divisional Target Dose−Excessive Dose Value. Instead, it may be defined: Corrected Dose value=Divisional Target Dose−Excessive Dose Estimation Value. At the second time of radiation, the controller outputs an interruption signal when the dose measured by the dose monitor reaches the corrected dose value.

11 Claims, 11 Drawing Sheets

(52) U.S. Cl.
CPC ......... *A61N 5/1067* (2013.01); *A61N 5/1077* (2013.01); *A61N 2005/1087* (2013.01)

(58) Field of Classification Search
USPC .......................................... 250/492.1–492.3
See application file for complete search history.

(56) References Cited

U.S. PATENT DOCUMENTS

| | | | |
|---|---|---|---|
| 2006/0027766 A1* | 2/2006 | Matsuda ................. | A61N 5/10 250/496.1 |
| 2006/0102856 A1 | 5/2006 | Matsuda et al. | |
| 2007/0114472 A1 | 5/2007 | Matsuda et al. | |
| 2007/0114473 A1 | 5/2007 | Matsuda et al. | |
| 2012/0187314 A1 | 7/2012 | Bert et al. | |
| 2016/0325116 A1* | 11/2016 | Sakamoto ............ | A61N 5/1043 |

FOREIGN PATENT DOCUMENTS

| | | | |
|---|---|---|---|
| JP | 2006-087649 A | 4/2006 | |
| JP | 3874766 B2 | 1/2007 | |
| JP | 2007-311125 A | 11/2007 | |
| JP | 2009-045229 A | 3/2009 | |
| JP | 2010-220975 A | 10/2010 | |
| JP | 2011-000378 A | 1/2011 | |

OTHER PUBLICATIONS

Japanese Office Action issued by the Japanese Patent Office dated Apr. 18, 2017 in corresponding Japanese Patent Application No. 2016-512539, with English translation (7 pages).
Communication and Supplementary Search Report dated Dec. 15, 2017 issued by the European Patent Office in the corresponding European Patent Application No. 14888873.8 (9 pages).

\* cited by examiner

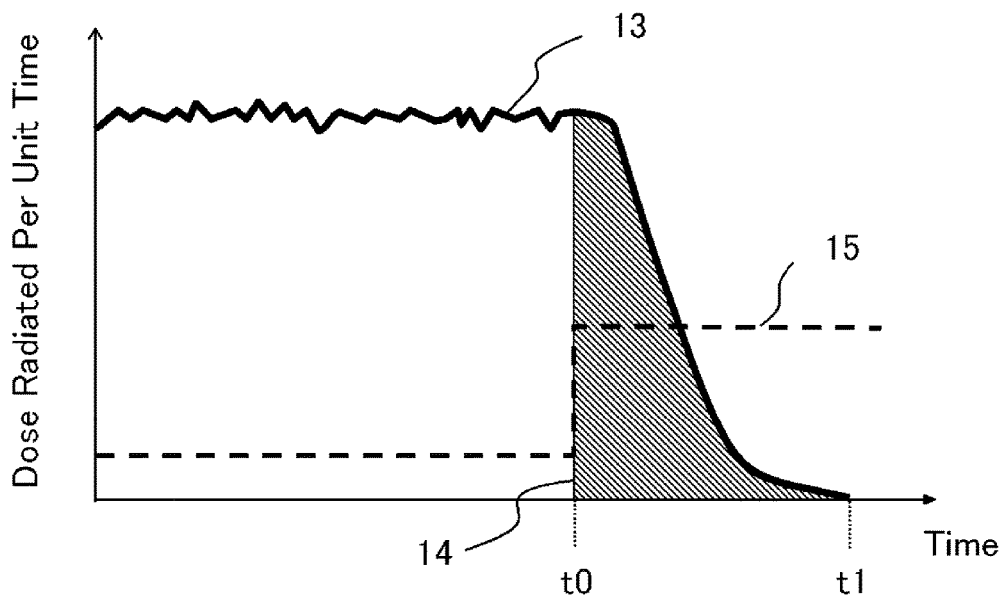

FIG. 6

| Irradiation Position Number | 1 | 2 | 3 | ... | i-1 | i | ... | m |
|---|---|---|---|---|---|---|---|---|
| First Divisional Target Dose Value | d1(1) | d1(2) | d1(3) | ... | d1(i-1) | d1(i) | ... | d1(m) |
| Second Divisional Target Dose Value | d2(1) | d2(2) | d2(3) | ... | d2(i-1) | d2(i) | ... | d2(m) |
| ... | ... | ... | ... | ... | ... | ... | ... | ... |
| k-th Divisional Target Dose Value | dk(1) | dk(2) | dk(3) | ... | dk(i-1) | dk(i) | ... | dk(m) |
| ... | ... | ... | ... | ... | ... | ... | ... | ... |
| n-th Divisional Target Dose Value | dn(1) | dn(2) | dn(3) | ... | dn(i-1) | dn(i) | ... | dn(m) |

| Irradiation Position Number | 1 | 2 | 3 | ... | i−1 | i | ... | m |
|---|---|---|---|---|---|---|---|---|
| First Divisional Target Dose Value | d1(1) | d1(2) | d1(3) | ... | d1(i−1) | d1(i) | ... | d1(m) |
| Second Divisional Target Dose Value | dd2(1) | dd2(2) | dd2(3) | ... | dd2(i−1) | d2(i) | ... | d2(m) |
| ... | ... | ... | ... | ... | ... | ... | ... | ... |
| k-th Divisional Target Dose Value | dk(1) | dk(2) | dk(3) | ... | dk(i−1) | dk(i) | ... | dk(m) |
| ... | ... | ... | ... | ... | ... | ... | ... | ... |
| n-th Divisional Target Dose Value | dn(1) | dn(2) | dn(3) | ... | dn(i−1) | dn(i) | ... | dn(m) |

| Irradiation Position Number | 1 | 2 | 3 | ... | i−1 | i | ... | m |
|---|---|---|---|---|---|---|---|---|
| Divisional Target Dose | d(1) | d(2) | d(3) | ... | d(i−1) | d(i) | ... | d(m) |
| Excessive-Dose Estimation Value | ee(1) | ee(2) | ee(3) | ... | ee(i−1) | ee(i) | ... | ee(m) |

| Irradiation Position Number | 1 | 2 | 3 | ... | i−1 | i | ... | m |
|---|---|---|---|---|---|---|---|---|
| Divisional Target Dose | d(1) | d(2) | d(3) | ... | d(i−1) | d(i) | ... | d(m) |
| Corrected Dose | dd(1) | dd(2) | dd(3) | ... | dd(i−1) | dd(i) | ... | dd(m) |

PARTICLE BEAM IRRADIATION APPARATUS

TECHNICAL FIELD

The present invention relates to a particle beam irradiation apparatus that radiates a particle beam to a diseased site, such as a cancer, to thereby perform its treatment, which is a particle beam irradiation apparatus to be used for performing radiation of the particle beam with a specified dose in conformity with a three-dimensional shape of the diseased site.

BACKGROUND ART

A particle beam therapy is a method for treating a cancer in such a manner that charged particles, such as protons or carbon ions, are accelerated to about several hundreds mega electronvolts by use of a device, such as an accelerator, which are then radiated to a patient to thereby give a dose to a tumor in the body. At this time, for the tumor, it is important to form a dose distribution that is as close as possible to a dose distribution ordered by a doctor, namely, a target distribution. In many cases, the target distribution is such a distribution in which the dose in the tumor is uniform and the dose outside the tumor is as lower as possible than in the tumor.

In general, when the particle beam accelerated by the accelerator is radiated to an object (including a case of human body), a three-dimensional dose distribution in the object has a feature of having a dose maximum peak at one given point. The dose maximum peak is called as a Bragg peak. Further, when it has a dose maximum peak at one point in a three-dimensional space, the position of such a peak is defined as "irradiation position" by that particle beam. In order to three-dimensionally form the target distribution using the particle beam with such a peak structure described above, some kind of ingenuity is required.

As one method for forming the target distribution, there is a scanning irradiation method. In order to employ this method, firstly, a feature is used that, using electromagnets, etc., arbitrarily deflects the particle beam in two directions perpendicular to a Z-direction that is a traveling direction of the particle beam, namely, X and Y-directions. Further, it is required to have a feature that adjusts energy of the particles to thereby arbitrarily adjust in the Z-direction, the position at which the Bragg peak is formed. Generally, a particle beam generation-transportation system that performs transportation and interruption of the accelerated particle beam is provided with the accelerator for accelerating the particle beam, and the accelerator also has an energy adjusting function. Then, upon setting a plurality of irradiation positions (referred to also as spots) in the tumor, the particle beam is radiated using the above two features, serially to the respective irradiation positions. The balance between the doses to be individually given to the respective irradiation positions has been adjusted and determined beforehand, so that the target distribution is formed as the result of totaling the respective dose distributions given to the respective irradiation positions.

Generally, the time taken to deflect the radiation direction of the particle beam in an X-Y direction to thereby move it from a given irradiation position to the next irradiation position, is 1 ms or shorter, and the time taken to move the position of the Bragg peak in the Z-direction by changing energy, is about 100 ms. Thus, generally, the irradiation sequence for the respective irradiation positions is such that, firstly, the particle beam is scanned with a single energy in an X-Y direction to thereby radiate the beam to all irradiation positions corresponding to that energy, and thereafter, the energy is changed to the next one.

At the time of movement of the irradiation position in the Z-direction by changing the energy, the radiation of the particle beam has to be always suspended, namely, interrupted. Depending on how to scan in the X-Y direction, the scanning irradiation method is subdivided further to the following respective methods.

The method in which the particle beam is interrupted during movement from a given irradiation position to the next irradiation position, is called as a spot scanning method, or a discrete spot-scanning method (see, for example, Patent Document 1, Patent Document 2).

For example, this method is achieved in such a manner that a feature of measuring the dose radiated to each irradiation position is provided, so that, at the time of reaching a predetermined dose value that is to be radiated to the irradiation position, the particle beam is interrupted and then the particle beam is moved to the next irradiation position.

In the case where the particle beam is not interrupted during movement from a given irradiation position to the next irradiation position, it is subdivided further to two methods. One of the methods is a method in which a feature of measuring the dose radiated to each irradiation position is provided, so that, at the time the dose reaches a specified value, the beam is scanned to the next irradiation position without interruption. This is called as a raster scanning method. Because irradiation is carried out during scanning of the particle beam, it is so adjusted that the total of the dose distribution given during the beam staying at the irradiation position and thus not being scanned, and the dose distribution given during being scanned, becomes the target distribution.

The other method in the case where the particle beam is not interrupted during scanning from a given irradiation position to the next irradiation position, is a line scanning method. This method is a method in which scanning is constantly continued, so that the particle beam is radiated to an irradiation target in such a manner that the particle beam does not stay at each irradiation position. A function of keeping constant a beam intensity that is a dose given per unit time and a function capable of arbitrarily changing a scanning speed are provided, so that, around the irradiation position where a large dose is to be given, the particle beam is scanned at a low speed, whereas around the irradiation position where a small dose is to be given, the particle beam is scanned at a high speed. In this manner, a final total dose distribution is adjusted to become the target distribution, by scanning the particle beam while adjusting the scanning speed to be inversely proportional to the dose to be given to each irradiation position.

According to the respective scanning irradiation methods mentioned above, because various uncertainties exist in actual irradiation, there is a possibility that, although the target distribution must be obtained on a calculation basis, the dose distribution actually obtained is not matched to the target distribution. The uncertainties include, for example, instability in intensity and/or position of the particle beam, an error in patient fixed position, an error in patient CT data, a signal delay and/or a noise of a control device, and the like. It is thought that, due to influence by them, an actual dose distribution possibly becomes different from the calculated values. Further, in the case where a tumor exists, in particular, in a respiratory organ, such as a liver, a lung, or the like, because the position of the tumor, the state around the tumor, or the like, changes temporally due to breathing of the patient, so that it is difficult to give a dose as planned to the diseased site.

As a method to solve the above problem, there is a method that is called as "rescan" or "repaint" as well (see, for example, Patent Document 1, Patent Document 2). This method is a method in which radiation of the particle beam to each irradiation position is performed plural times in a divided manner. This method is based on an idea of totaling the dose distributions at the plural times to average the errors therein to thereby cause error reduction. The number of divided times is called as a number of rescan times. The irradiation sequence is such that, firstly, the particle beam is scanned with a given energy in the X-Y direction to thereby radiate the beam once to all irradiation positions corresponding to that energy. Thereafter, radiation is performed again to each irradiation position without changing the energy. This is repeated the number of rescan times, and, after irradiating the number of rescan times, the energy is changed to the next one. The number of rescan times may differ depending on the energy, or may be the same for all of the energies. Generally, as the number of rescan times is increased, the influence by the above errors is averaged to become smaller.

CITATION LIST

Patent Document

Patent Document 1: Japanese Patent No. 3874766 (FIG. 1, FIG. 7)
Patent Document 2: Japanese Patent No. 3737098 (FIG. 1, FIG. 7)

SUMMARY OF THE INVENTION

Problems to be Solved by the Invention

The rescan is applicable to any one of the spot scanning method, the raster scanning method and the line scanning method. In the case of anyone of them, when the number of rescan times is increased, the dose value to be radiated per one time to each irradiation position has to be made small, accordingly.

In the spot scanning method, the beam is interrupted after the dose value to be radiated per one time is given to each irradiation position; however, there is always a time difference that is not zero (approximately, about several tens to several hundreds of microseconds) from when the apparatus judges that the dose value to be radiated has been given until the beam is actually interrupted, so that the dose radiated in such a time range is given to the patient as an excessive dose (unplanned dose).

Further, there is a problem that the value of the above excessive dose becomes larger as the number of rescan times is increased.

Accordingly, an object of this invention is to significantly reduce, in the spot scanning method, the total amount of plural times of excessive doses due to delay of beam interruption.

Means for Solving the Problems

The particle beam irradiation apparatus of the invention is a particle beam irradiation apparatus which includes: a particle beam generation-transportation system that performs transportation and interruption of an accelerated particle beam; a scanning device that deflects the particle beam transported from the particle beam generation-transportation system in two directions perpendicular to a traveling direction of the beam, to thereby move from one to another of irradiation positions at which an irradiation target is irradiated; a controller that controls the particle beam generation-transportation system and the scanning device; and a dose monitor that measures a dose of the particle beam; wherein the particle beam is radiated plural times to each said irradiation position, and the particle beam is interrupted at the time the irradiation position is being moved. The particle beam irradiation apparatus of the invention further includes a storage unit in which positional information of the irradiation position and a divisional target dose that is a dose radiated per one time to the irradiation position, are to be stored, so that the dose monitor, when the measured dose reaches a value of the divisional target dose, measures an excessive dose radiated from when reaching to that value until radiation of the particle beam is interrupted. The controller of the particle beam irradiation apparatus of the invention is characterized in that: at a first time of radiation to each said irradiation position, it controls the particle beam generation-transportation system and the scanning device to repeat, for up to a last said irradiation position at a same depth in the irradiation target, an operation in which, when the measured dose with respect to one said irradiation position measured by the dose monitor reaches the value of the divisional target dose, the particle beam generation-transportation system interrupts radiation of the particle beam and the scanning device performs deflection control corresponding to a next said irradiation position and thereafter, the particle beam generation-transportation system restarts radiation of the particle beam; and at a second or later time of radiation to each said irradiation position, it controls the particle beam generation-transportation system and the scanning device to repeat just a predetermined number of times, for every said irradiation position at a same depth in the irradiation target, an operation in which, when the measured dose with respect to one said irradiation position measured by the dose monitor reaches a corrected dose value resulted from subtracting a value of the excessive dose at a previous time at that irradiation position from the value of the divisional target dose, the particle beam generation-transportation system interrupts radiation of the particle beam and the scanning device performs deflection control corresponding to a next said irradiation position and thereafter, the particle beam generation-transportation system restarts radiation of the particle beam.

Effect of the Invention

According to the particle beam irradiation apparatus of the invention, at the second or later time of radiation, the particle beam is interrupted based on the corrected dose value resulted from subtracting the value of the excessive dose at the previous time at that irradiation position from the value of the divisional target dose, so that it is possible to significantly reduce, in the spot scanning method, the total amount of plural times of excessive doses due to delay of beam interruption.

BRIEF DESCRIPTION OF THE DRAWINGS

FIG. 3 is a diagram illustrating an excessive dose at the time of beam interruption.

FIG. 4 is a table briefly illustrating an example of information stored in a storage unit in FIG. 1.

FIG. 5 is a table briefly illustrating an example of information during irradiation stored in the storage unit in FIG. 1.

FIG. 6 is a table briefly illustrating an example of information stored in a storage unit according to Embodiment 2 of the invention.

FIG. 7 is a table briefly illustrating an example of information during irradiation stored in the storage unit according to Embodiment 2 of the invention.

FIG. 12 is a table briefly illustrating an example of information stored in a storage unit according to Embodiment 5 of the invention.

FIG. 13 is a table briefly illustrating another example of information stored in the storage unit according to Embodiment 5 of the invention.

MODES FOR CARRYING OUT THE INVENTION

Embodiment 1

Figure 1:
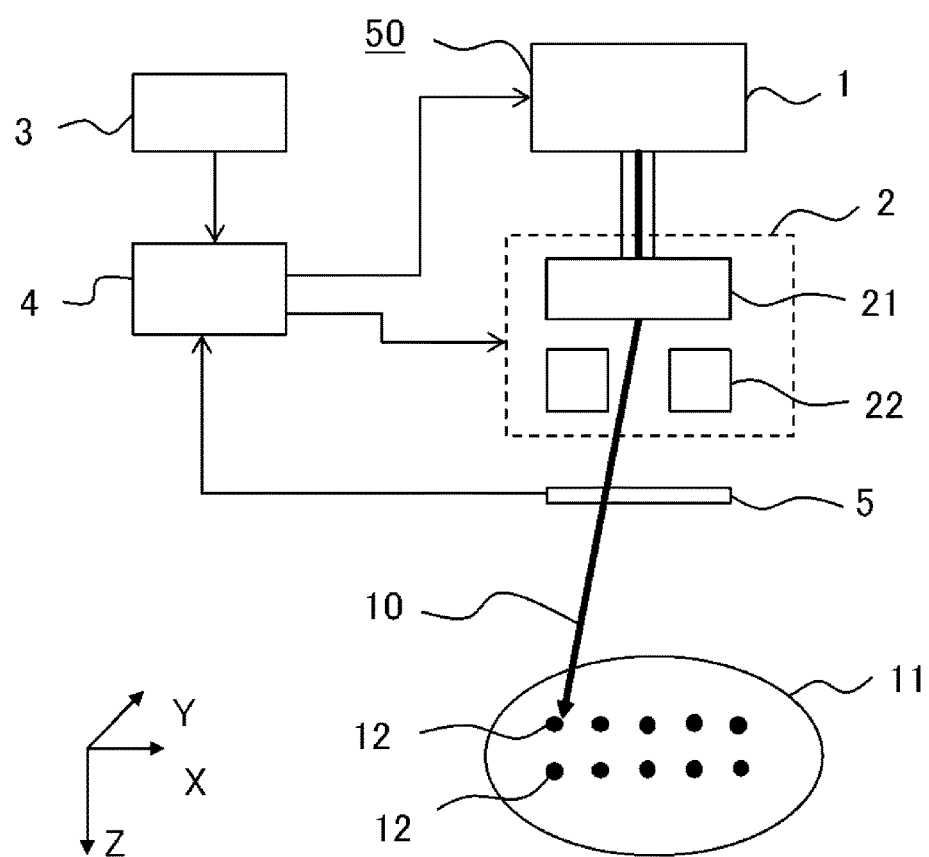
FIG. 1 is a schematic configuration diagram of a particle beam irradiation apparatus according to Embodiment 1 of the invention.

FIG. 1 is a schematic configuration diagram of a particle beam irradiation apparatus according to Embodiment 1 of the invention.

A particle beam irradiation apparatus 50 according to Embodiment 1 of the invention includes: a particle beam generation-transportation system 1 that accelerates charged particles up to a required energy to thereby generate accelerated charges particles as a particle beam 10, and then transports it to a scanning device 2; and the scanning device 2 that deflects the particle beam 10 generated by the particle beam generation-transportation system 1 in two directions perpendicular to a Z-direction that is a traveling direction of the particle beam, namely, X and Y-directions, to thereby causing the beam to scan at arbitrary positions in a patient's tumor, that is, an irradiation target 11. Generally, the particle beam generation-transportation system 1 includes an accelerator for accelerating the charged particles and a transport system for transporting the particle beam 10 from the accelerator to the scanning device 2. The scanning device 2 includes an X-direction scanning device 21 for deflecting the particle beam 10 in the X-direction and a Y-direction scanning device 22 for deflecting the particle beam 10 in the Y-direction.

Furthermore, the particle beam irradiation apparatus 50 includes: a storage unit 3 in which positional information of each irradiation position 12 in the irradiation target 11, each dose value of the particle beam 10 to be radiated to each irradiation position 12, information of scanning speed by the scanning device 2 and the like, are to be stored; a controller 4 that controls starting of emission of the particle beam 10 and its interruption by the particle beam generation-transportation system 1, as well as controls scanning of the particle beam 10 by the scanning device 2; and a dose monitor 5 that measures a dose value due to radiation of the particle beam 10 scanned by the scanning device 2 to each irradiation position 12 in the irradiation target 11. Note that, examples of the positional information of each irradiation position 12 to be stored in the storage unit 3 include: an irradiation position number; information of a position in an X-Y coordinate system of each irradiation position 12; excitation current values for the scanning electromagnets in the scanning device 2 for deflecting the particle beam 10 to an X-posit ion and a Y-position of each irradiation position 12; an energy corresponding to the Z-position of each irradiation position 12; and the like.

When the energy of the particle beam 10 is set to a given energy and the particle beam 10 is radiated while being moved in an X-Y direction using the radiation method as described above, an X-Y two-dimensional diseased region at a given depth, namely, at a given Z-position in the diseased site can be irradiated with the particle beam 10. According to the invention, an X-Y two-dimensional diseased region is irradiated plural times at the same Z-position with the particle beam 10 having a single energy, namely, a rescan is performed.

Figure 2A:
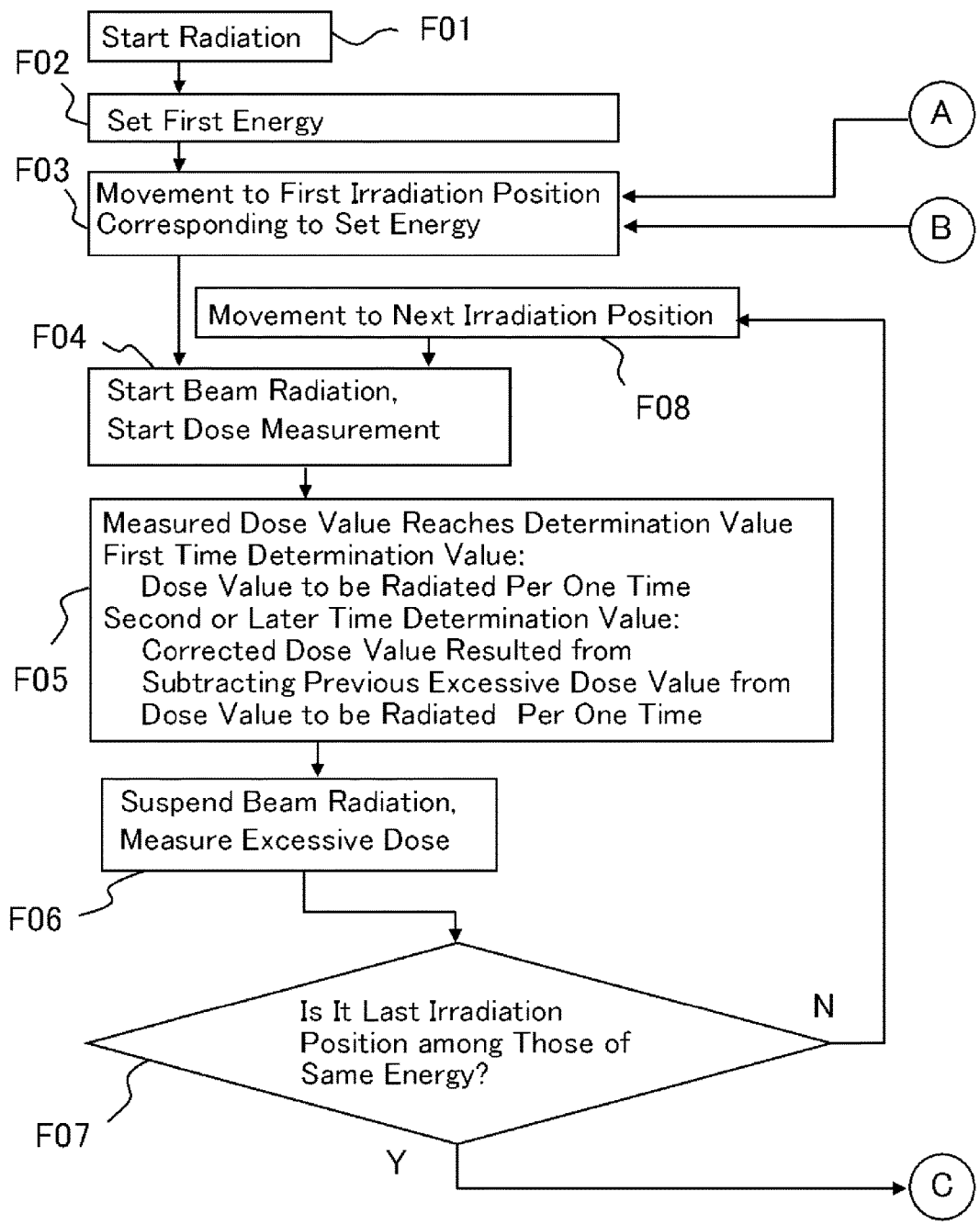
FIG. 2A and FIG. 2B are a set of flowchart showing operations of the particle beam irradiation apparatus of FIG. 1.
Figure 2B:
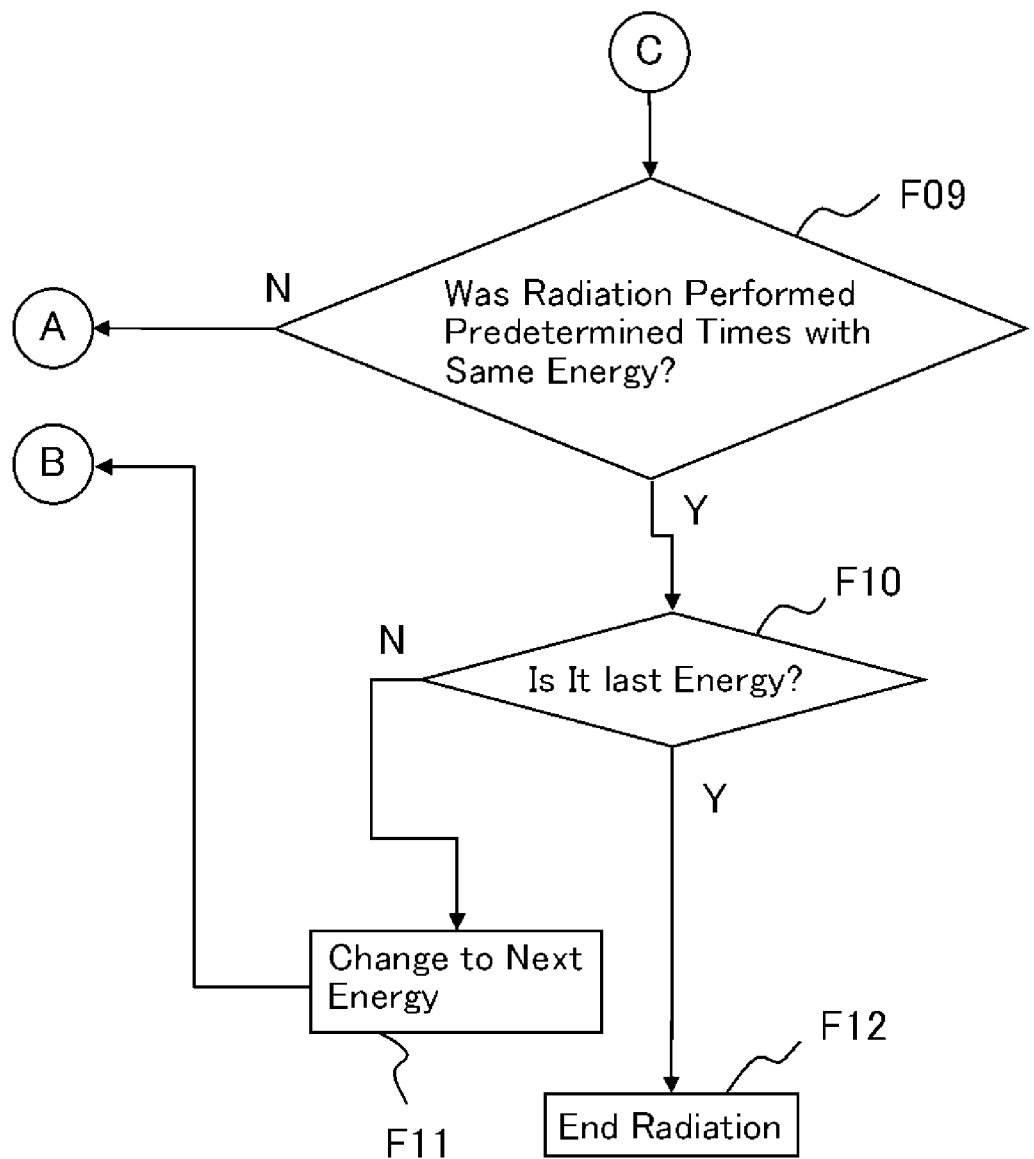

A rescan operation by the particle beam irradiation apparatus 50 of the invention will be described using FIG. 2A and FIG. 2B. FIG. 2A and FIG. 2B are a set of flowchart showing operations of the particle beam irradiation apparatus of FIG. 1. The operation of irradiation is started in Step F01. First, the parameters of the particle beam generation-transportation system 1 are set so that the energy of the particle beam 10 becomes the first energy for radiation (Step F02). Further, the parameters of the scanning device 2 are set so that the irradiation position 12 of the particle beam 10 becomes the first irradiation position 12 corresponding to the first energy (Step F03). Thereafter, the particle beam 10 is generated to thereby start radiation, and at the same time, to start measurement of the dose by the dose monitor 5 (Step F04). In Step F05, it is determined whether or not the value of the measured dose reaches a determination value stored in the storage unit 3.

In the case of the first time of radiation to a given irradiation position 12, when the value of the measured dose (measured dose value) reaches the value of a divisional target dose (divisional target dose value) that is the value of a target dose (target dose value) per one time and is stored in the storage unit 3 (Step F05), the controller 4 issues an instruction for interruption to the particle beam generation-transportation system 1, so that the particle beam generation-transportation system 1 interrupts the particle beam 10 (Step F06). At the first time of radiation, the determination value for determining whether to interrupt the particle beam 10 is the divisional target dose value corresponding to each irradiation position 12. On this occasion, in Step F06, because there is a time lag, as shown in FIG. 3, from when the measured dose value at that irradiation position 12 reaches the target dose value per one time until the particle beam 10 is actually interrupted, a dose value radiated during the time lag, that is, the value of an excessive dose 14, is measured by the dose monitor 5 (Step F06). The time lag is generally shorter than 1 msec.

FIG. 3 is a diagram illustrating an excessive dose at the time of beam interruption. The abscissa represents time and the ordinate represents a dose radiated per unit time. In FIG. 3, an interruption signal 15 is also shown that provides an instruction for interrupting the particle beam 10. When the interruption signal 15 rises at Time t0, an instruction for interrupting the particle beam 10 is issued, so that a dose distribution 13 becomes zero at Time t1 that is just after the elapse of a time of the time lag. In FIG. 3, the value of total dose from Time t0 to Time t1 is the value of the excessive dose 14.

In Step F07, it is confirmed whether or not the irradiation position 12 is the last irradiation position among those of the same energy, and if the irradiation position 12 is not the last irradiation position among those of the same energy, the flow moves to Step F08. In Step F08, the controller 4 issues an instruction for movement to the next irradiation position 12. After completion of movement to the next irradiation position 12, the controller 4 executes Step F05 and Step F06.

When it is confirmed in Step F07 whether or not the irradiation position 12 is the last irradiation position among those of the same energy, if this shows that radiation has been once completed for all the irradiation positions 12 corresponding to a given energy, the flow moves to Step F09. In Step F09, it is determined whether or not radiation has been performed a specified number of rescan times, and if radiation by the specified number of rescan times has not been completed, the flow returns to Step F03, so that a second time or a third time to an n-th time (last time) of irradiation is performed for the respective irradiation positions 12 of the same energy. In Step F09, if radiation by the specified number of rescan times (n times) has been completed, the flow moves to Step F10.

In the case of second or later time of radiation to a given irradiation position 12, when, in Step F05, the measured dose value reaches a value (corrected dose value) that is smaller, just by a value of the excessive dose measured at the previous time of radiation to the same irradiation position 12 (in previous Step F06), than the target dose value per one time (divisional target dose value) stored in the storage unit 3, the controller 4 issues an instruction for interruption to the particle beam generation-transportation system 1 in Step F06, so that the particle beam generation-transportation system 1 interrupts the particle beam 10. Even at this time, like at the first time of radiation, an excessive dose radiated in a period until the particle beam 10 is actually interrupted is measured. At the second time of radiation, the determination value for determining whether to interrupt the particle beam 10 is the corrected dose value corresponding to each irradiation position 12. For example, the corrected dose value for causing interruption with respect to the irradiation position 12 of an irradiation position number i is represented by d(i)-e(i). Here, d(i) is the divisional target dose value at the irradiation position 12 of the irradiation position number i; e(i) is the value of the excessive dose (excessive dose value) measured at the first time, namely, at the previous time, at the irradiation position 12 of the irradiation position number i. Thereafter, the flow from Step F03 to Step F09 is repeated similarly, to thereby perform radiation to all the irradiation positions 12 of the same energy.

In Step F09, when radiation is completed n-number of times that is a specified number of rescan times, to all the irradiation positions 12 corresponding to that energy, the flow moves to Step F10. In Step F10, it is determined whether or not the energy is the last energy, and if it is not the last energy, the flow moves to Step F11. In Step F11, the parameters of the particle beam generation-transportation system 1 are changed so that the energy of the particle beam 10 becomes the next energy. Until it is determined in Step F10 that the energy is the last one, the flow from Step F03 to Step F11 is repeated to thereby repeat similar radiation, so that one-time therapy is completed (Step F12).

At the second or later time of rescan, in order for the controller 4 to determine whether or not the measured dose value with respect to a given irradiation position 12 reaches the value that is smaller, just by the excessive dose value measured at the previous time of radiation to the same irradiation position 12, than the target dose value per one time (divisional target dose value) stored in the storage unit 3, it is required to retain information related to the excessive dose in some way from when the excessive dose to the given irradiation position 12 is measured until the next time of radiation is performed to the same irradiation position 12.

Examples of the configuration of the storage unit 3 for that purpose are shown in FIG. 4 and FIG. 5. FIG. 4 is a table briefly illustrating an example of information stored in the storage unit in FIG. 1, and FIG. 5 is a table briefly illustrating an example of information during irradiation stored in the storage unit in FIG. 1. In the storage unit 3, there are reserved memory regions for storing an irradiation position number, a target dose per one time of rescan (divisional target dose) and an excessive dose, for every irradiation position 12. As shown in FIG. 4, it is assumed that, in initial-state memory information 33, there is stored 0 (zero) as each excessive dose before starting radiation. Shown in FIG. 4 and FIG. 5 are examples for the irradiation position number from 1 to m. In "Divisional Target Dose" and "Excessive Dose" in the storage unit 3, m-pieces of data each corresponding to the irradiation position number are stored, respectively. The memory regions in which stored is m-number of divisional target doses are divisional target-dose storing regions, and the memory regions in which stored ism-number of excessive doses are excessive-dose storing regions. Note that, actually, other than the irradiation position number, the divisional target dose and the excessive dose, there are also stored in the storage unit 3, energy information, coordinate information of the irradiation position 12, excitation current values for the electromagnets in the scanning device 2 that correspond to said position, and the like; however, here, they are omitted from description.

At the first time of radiation to each irradiation position 12, when the excessive dose is measured from when the radiation dose value reaches the target dose value until the particle beam 10 is actually interrupted, as shown in memory information 34, the excessive dose value corresponding to that irradiation position 12 is overwritten. In FIG. 5, at every time the excessive dose is measured, the excessive dose value corresponding to that irradiation position 12 is overwritten, so that the measured excessive values e(1) to e(i−1) are recorded in an area 44a in which the irradiation position number is from 1 to i−1. In an area 44b in which the irradiation position number is from i to m, the excessive dose values remain the same as zero. In a state after completion of radiation once to all the irradiation positions 12, the values of the excessive doses are being recorded one by one for all the irradiation positions 12.

Then, at the second time of radiation to a given irradiation position 12, the controller 4 reads out from the storage unit 3, respectively, the target dose value per one time (divisional target dose value) and the excessive dose value with respect to that irradiation position 12, to thereby calculate the corrected dose value that is a difference between them, and, at the time the radiation dose value reaches the corrected dose value, performs control to interrupt the particle beam 10 and to move the position to the next irradiation position 12. For example, the determination value for performing interruption with respect to the irradiation position 12 of the irradiation position number i, is a corrected dose value represented by d(i)-e(i). In this manner, the particle beam irradiation apparatus 50 of Embodiment 1 performs radiation of the particle beam 10 while repeating an operation to store the excessive dose value measured at (k−1)-th time of radiation to a given irradiation position 12, and, at k-th time of radiation to the same irradiation position 12, to interrupt the particle beam 10 and to move the position to the next irradiation position 12 at the time the radiation dose value reaches the corrected dose value that is a difference between the target dose value (divisional target dose value) and the excessive dose value at (k−1)-th time.

As described above, because of the provision of the storage unit 3 with the configuration as shown in FIG. 4 and FIG. 5, the particle beam irradiation apparatus 50 of Embodiment 1 can negate at k-th time radiation, the excessive dose value radiated at (k−1)-th time. Heretofore, since an excessive dose occurs every time of rescan, when the excessive dose value per one time is defined as E, an excessive dose value of E×n is verified at the last time in n-number of rescans. In contrast, the particle beam irradiation apparatus 50 of Embodiment 1 can suppress the conventional excessive dose value that occurs every time of rescan, into just one E at the last time of rescan, making it possible to reduce the total excessive dose value to 1/n of the conventional value. Because the particle beam irradiation apparatus 50 of Embodiment 1 can increase the number of rescan times without a risk of increasing the excessive dose, it is possible to perform radiation with radiation-dose accuracy that is higher than that in the conventional case.

Here, it has been assumed that the total dose to be radiated to each irradiation position 12 is equally divided by the number of total rescan times; however, in principle, so far as each total dose value for each irradiation position 12 is kept the same, the dose distribution finally obtained in the irradiation target 11 is the same even if the total dose has been divided in any ratio in each rescan time. Thus, it is not a necessary condition that the value of the target dose per one time for a given irradiation position 12 is the same each time for every number of rescans. However, essentially, the object of rescan is to divide and thus to average the influence on the dose distribution by an unpredictable irradiation error, such as, due to a motion associated with the breathing, the cough, etc. of the patient as the irradiation target 11. Accordingly, without any particular reason, it is thought to be preferable that the value of the target dose per one time for a given irradiation position 12 be the same each time for every number of rescans. If assuming that the target dose per one time is the same each time for every number of rescans, it is possible to reduce the memory capacity to be used, by applying the configuration of the storage unit 3 as shown in FIG. 4 and FIG. 5.

As described above, the particle beam irradiation apparatus 50 of Embodiment 1 is a particle beam irradiation apparatus which comprises: the particle beam generation-transportation system 1 that performs transportation and interruption of the accelerated particle beam 10; the scanning device 2 that deflects the particle beam. 10 transported from the particle beam generation-transportation system 1 in two directions perpendicular to a traveling direction of the beam, to thereby move from one to another of irradiation positions 12 at which the irradiation target 11 is irradiated; the controller 4 that controls the particle beam generation-transportation system 1 and the scanning device 2; and the dose monitor 5 that measures a dose of the particle beam 10; wherein the particle beam 10 is radiated plural times to each irradiation position 12, and the particle beam 10 is interrupted at the time the irradiation position 12 is being moved. The particle beam irradiation apparatus 50 of the invention further includes the storage unit 3 in which positional information of the irradiation position 12 and a divisional target dose that is a dose to be radiated per one time to the irradiation position 12, are to be stored, wherein the dose monitor 5, when the measured dose reaches a value of the divisional target dose, measures an excessive dose 14 radiated from when reaching to that value until radiation of the particle beam 10 is interrupted. The controller 4 of the particle beam irradiation apparatus 50 of the invention is characterized in that:

at the first time of radiation to each irradiation position 12, it controls the particle beam generation-transportation system 1 and the scanning device 2 to repeat, for up to the last irradiation position 12 at the same depth in the irradiation target 11, an operation in which, when the measured dose with respect to one irradiation position 12 measured by the dose monitor 5 reaches the value of the divisional target dose, the particle beam generation-transportation system 1 interrupts radiation of the particle beam 10 and the scanning device 2 performs deflection control corresponding to the next irradiation position 12 and thereafter, the particle beam generation-transportation system 1 restarts radiation of the particle beam 10; and at a second or later time of radiation to each irradiation position 12, it controls the particle beam generation-transportation system 1 and the scanning device 2 to repeat just a predetermined number of times, for every irradiation position 12 at the same depth in the irradiation target 11, an operation in which, when the measured dose with respect to one said irradiation position 12 measured by the dose monitor 5 reaches a corrected dose value resulted from subtracting a value of the excessive dose 14 at the previous time at that irradiation position from the value of the divisional target dose, the particle beam generation-transportation system 1 interrupts radiation of the particle beam 10 and the scanning device 2 performs deflection control corresponding to the next irradiation position 12 and thereafter, the particle beam generation-transportation system 1 restarts radiation of the particle beam 10. Thus, at the second or later time of radiation, the particle beam 10 is interrupted based on the corrected dose value resulted from subtracting the value of the excessive dose 14 at the previous time at that irradiation position from the value of the divisional target dose, so that it is possible, in the spot scanning method, to significantly reduce the total amount of plural times of the excessive doses 14 due to delay of beam interruption, in comparison to the conventional case.

Embodiment 2

In Embodiment 1, description has been made about a configuration example of the storage unit 3 with the assumption that the total dose to be radiated to each irradiation position 12 is equally divided by the number of total rescan times. However, if it is intended to make the divisional target dose value that is the value of the target dose per one time, different each time for every number of rescans, it is impossible to get this by the configuration of the storage unit 3 as shown in FIG. 4 and FIG. 5. In Embodiment 2, a configuration example of the storage unit 3 that can make the divisional target dose value different each time for every number of rescans, will be described.

FIG. 6 is a table briefly illustrating an example of information stored in a storage unit according to Embodiment 2 of the invention, and FIG. 7 is a table briefly illustrating an example of information during irradiation stored in the storage unit according to Embodiment 2 of the invention. It is assumed that, in the initial state, the storage unit 3 of Embodiment 2 is storing, for each irradiation position 12, an irradiation position number and every divisional target dose value at each time in a total n-number of rescans. Shown in FIG. 6 and FIG. 7 are examples for the irradiation position number from 1 to m. In the storage unit 3, the divisional target dose values for the total n-number of rescans are stored as m-pieces of data corresponding to the respective irradiation position numbers. As shown in initial-state memory information 35, the first divisional target dose values for the irradiation position number from 1 to m are d1(1) to d1(m), respectively. The k-th divisional target dose values for the irradiation position number from 1 to m are dk(1) to dk(m), respectively. The memory regions in which stored is (m× k) number of divisional target doses are divisional target-dose storing regions. In the case of making the divisional target dose value different each time for every number of rescans, the values from the first divisional target value d1(i) to the n-th divisional target dose value dn(i) are set different to each other, and the divisional target dose value each time may be set freely. With the assumption like in Embodiment 1 that the total dose to be radiated to each irradiation position 12 is equally divided by the number of total rescans times, the divisional target dose value per one time for a given irradiation position 12 becomes the same value at any time of rescan.

Operations of the particle beam irradiation apparatus 50 of Embodiment 2 will be described. At the first time of radiation to each irradiation position 12, when the excessive dose in a period from when the radiation dose value reaches the divisional target dose value until the particle beam 10 is actually interrupted is measured, as shown in memory information 36, the divisional target dose value for the second time of rescan at that irradiation position 12 is overwritten by a value that is smaller just by the value of the excessive dose than the original value. In FIG. 7, at every time the excessive dose is measured, the divisional target dose value corresponding to that irradiation position 12 for the next time is overwritten, so that the corrected dose values from dd2(1) to dd2 (i−1), each being the next divisional target dose value, are recorded in an area 46a in which the irradiation position number is from 1 to i−1. Here, the corrected dose value dd2(1) is resulted from subtracting the measured excessive dose value e(1) from the original divisional target dose value d2(1). The corrected dose value dd2(i−1) is resulted from subtracting the measured excessive dose value e(i−1) from the original divisional target dose value d2(i−1). The divisional target dose values for the second time for the irradiation position number from i to m, remain the same as the original divisional target dose value d2(i) to the original divisional target dose value d2(m).

In a state after completion of radiation once to all the irradiation positions 12, the values of the divisional target doses for the second time of rescan for all the irradiation positions 12 are being overwritten. Then, at the second time of radiation, the corrected dose values dd2(1) to dd2(m), each being the rewritten divisional target dose value, are read out, and such control is performed that, at the time the radiation dose value reaches that corrected dose value, the particle beam 10 is interrupted and the position is moved to the next irradiation position 12. In this manner, the particle beam irradiation apparatus 50 of Embodiment 2 performs radiation of the particle beam 10 while repeating an operation: to perform rewriting with the corrected dose value that is resulted from subtracting the excessive dose value measured at (k−1)-th time of radiation to a given irradiation position 12 from k-th time divisional target dose value for the same irradiation position 12; and, at k-th time of radiation to the same irradiation position 12, to interrupt the particle beam 10 and move the position to the next irradiation position 12 at the time the radiation dose value reaches the rewritten corrected dose value.

Like Embodiment 1, the particle beam irradiation apparatus 50 of Embodiment 2 can suppress the conventional excessive dose value that occurs every time of rescan, into just one E at the last time of rescan, making it possible to reduce the total excessive dose value to 1/n of the conventional value. Thus, it is possible in the spot scanning method to significantly reduce the total amount of plural times of the excessive doses due to delay of beam interruption, in comparison to the conventional case. Because the particle beam irradiation apparatus 50 of Embodiment 2 can increase the number of rescan times without a risk of increasing the excessive dose, it is possible to perform radiation with radiation-dose accuracy that is higher than that in the conventional case. Further, the particle beam irradiation apparatus 50 of Embodiment 2 can set the value of divisional target dose to be different each time for every number of rescans, making it easier to finely adjust the divisional target dose.

Embodiment 3

The configuration of the storage unit 3 may be other than the configurations in Embodiment 1 and Embodiment 2.

Figure 8:
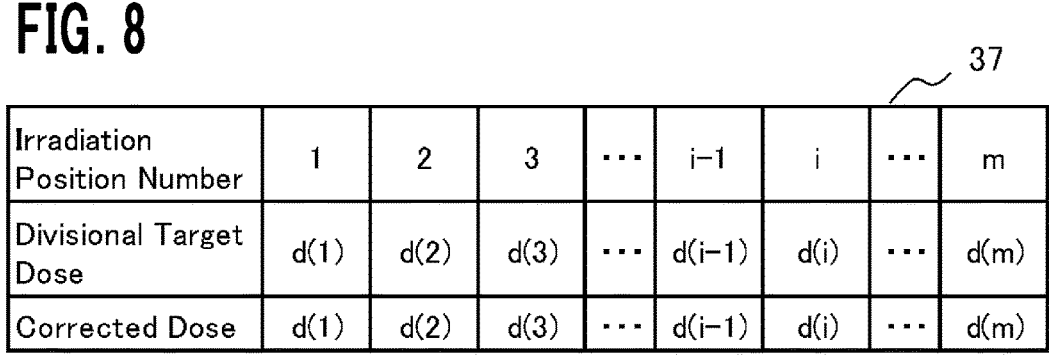
FIG. 8 is a table briefly illustrating an example of information stored in a storage unit according to Embodiment 3 of the invention.
Figure 9:
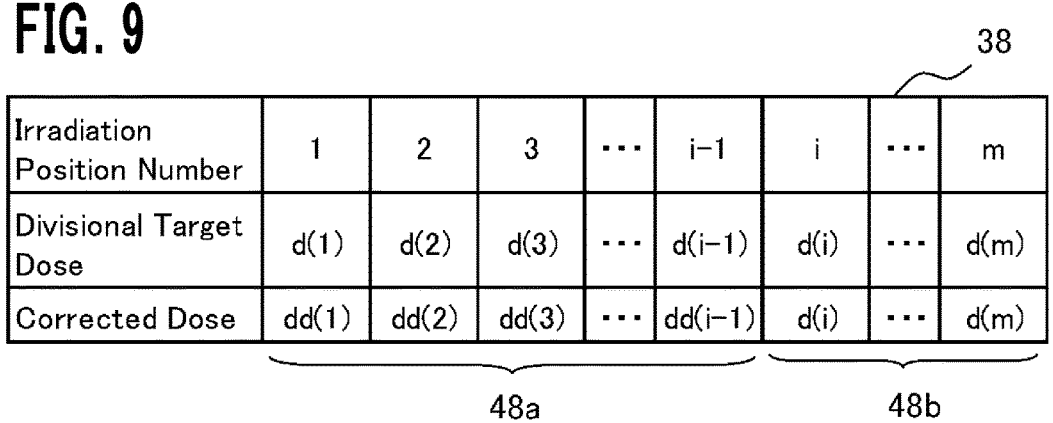
FIG. 9 is a table briefly illustrating an example of information during irradiation stored in the storage unit according to Embodiment 3 of the invention.

FIG. 8 is a table briefly illustrating an example of information stored in a storage unit according to Embodiment 3 of the invention, and FIG. 9 is a table briefly illustrating an example of information during irradiation stored in the storage unit according to Embodiment 3 of the invention. It is assumed that, in the storage unit 3 of Embodiment 3, there are reserved memory regions for storing an irradiation position number, a target dose per one time of rescan (divisional target dose) and a corrected dose as a revised target dose, for every irradiation position 12, and in the initial state before radiation, as each value in "Corrected Dose", a value that is the same as the target dose value per one time of scan (divisional target dose) is stored. Shown in FIG. 8 and FIG. 9 are examples for the irradiation position number from 1 to m. As shown in initial-state memory information 37, in the storage unit 3, the divisional target doses and the corrected doses are also stored as respective m-pieces of data corresponding to the respective irradiation position numbers. The memory regions in which stored is m-number of divisional target doses are divisional target-dose storing regions, and the memory regions in which stored is m-number of corrected doses are determination-value storing regions.

Operations of the particle beam irradiation apparatus 50 of Embodiment 3 will be described. At the first time of radiation to each irradiation position 12, the controller 4 reads out the value of the corrected dose (corrected dose value) and, when the value of radiation dose reaches the corrected dose value, interrupts the particle beam 10 and moves the position to the next irradiation position 12. On this occasion, when the excessive dose in a period from when the value of the radiation dose reaches the corrected dose value until the particle beam 10 is actually interrupted, is measured, as shown in memory information 38, the value of the corrected dose for that irradiation position 12 is rewritten with a value that is smaller just by this excessive dose value than the divisional target dose value. In FIG. 9, at every time the excessive dose is measured, the value of the corrected dose corresponding to that irradiation position 12 is overwritten, so that the corrected dose values from dd(1) to dd(i−1) are recorded in an area 48a in which the irradiation position number is from 1 to i−1. The corrected dose value dd(1) is resulted from subtracting the measured excessive dose value e(1) from the initial value of the corrected dose d(1). The corrected dose value dd (i−1) is resulted from subtracting the measured excessive dose value e(i−1) from the initial value of the corrected dose d(i−1). In an area 48b in which the irradiation position number is from i to m, the corrected dose values remain the same as those of initial d(i) to d(m). In a state after completion of radiation once to all the irradiation positions 12, the values of the corrected doses for all the irradiation positions 12 are being revised based on the actually-measured excessive dose values.

In this manner, the particle beam irradiation apparatus 50 of Embodiment 3 performs radiation of the particle beam 10 while repeating an operation: to perform rewriting with the value that is resulted from subtracting the excessive dose value measured at (k−1)-th time of radiation to a given irradiation position 12 from the divisional target dose value per one time, namely, with the value of the corrected dose for the same irradiation position 12; and at k-th time of radiation to the same irradiation position 12, to interrupt the particle beam 10 and move the position to the next irradiation position 12 at the time the value of the radiation dose reaches the corrected dose value. Note that, because the first corrected dose value is the same as the divisional target dose value, the particle beam irradiation apparatus 50 of Embodiment 3 performs radiation with the operations that are the same as those in the flowchart of FIGS. 2A&2B.

Like Embodiment 1, the particle beam irradiation apparatus 50 of Embodiment 3 can suppress the conventional excessive dose value that occurs every time of rescan, into just one E at the last time of rescan, making it possible to reduce the total excessive dose value to 1/n of the conventional value. Thus, it is possible in the spot scanning method to significantly reduce the total amount of plural times of the excessive doses due to delay of beam interruption, in comparison to the conventional case. Because the particle beam irradiation apparatus 50 of Embodiment 3 can increase the number of rescan times without a risk of increasing the excessive dose, it is possible to perform radiation with radiation-dose accuracy that is higher than that in the conventional case.

Like the particle beam irradiation apparatus 50 of Embodiment 1, the particle beam irradiation apparatus 50 of Embodiment 3 can reduce the memory capacity to be used in comparison to the particle beam irradiation apparatus 50 of Embodiment 2.

Embodiment 4

Figure 10:
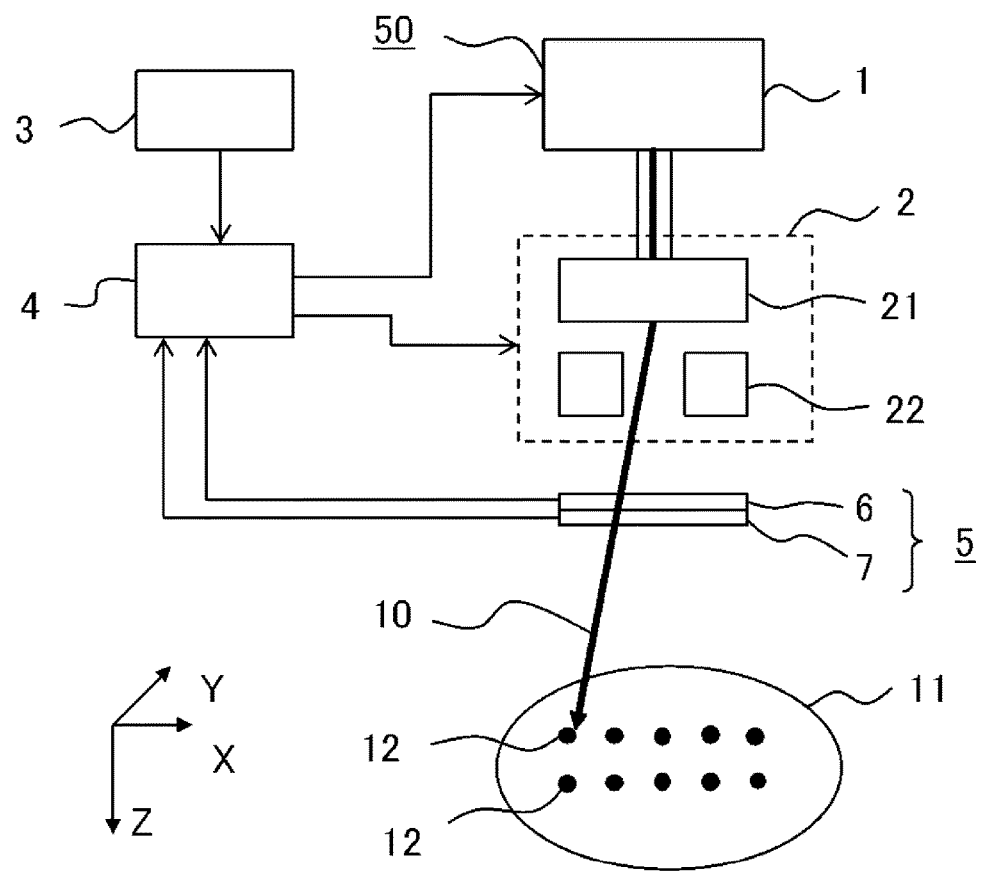
FIG. 10 is a schematic configuration diagram of a particle beam irradiation apparatus according to Embodiment 4 of the invention.

In Embodiments 1 to 3, description has been made using the case where the dose monitor 5 is provided with a single monitor part for measuring the dose; however, as shown in FIG. 10, the dose monitor 5 may be provided with two monitor parts of a first monitor part 6 and a second monitor part 7. FIG. 10 is a schematic configuration diagram of a particle beam irradiation apparatus according to Embodiment 4 of the invention. In some cases, there is a concern about a dead time or the like at the time of switching of dose measurement control using the single monitor part. When dose measurement is performed for a given irradiation position 12 using the first monitor part 6 until the radiation dose value reaches the target dose value, and after reaching, the excessive dose value in a period until the beam is actually interrupted is measured using the second monitor part 7, this makes it possible to highly accurately measure the excessive dose. The particle beam irradiation apparatus 50 of Embodiment 4 can measure the excessive dose more highly accurately than the particle beam irradiation apparatuses 50 of Embodiment 1 to 3 and thus can perform radiation with much higher radiation-dose accuracy.

Embodiment 5

In Embodiments 1 to 4, there is shown such a radiation method in which the excessive dose value at the interruption of the particle beam 10 has been measured, and the next-time radiation is performed to a little less extent corresponding to that value; however, though depending on the specification of the accelerator in the particle beam generation-transportation system 1, there are cases where the relationship between time and an imparted dose (imparted dose characteristic) as shown in FIG. 3 is highly reproducible, so that the excessive dose value at the interruption of the particle beam 10 can be estimated beforehand. For example, it is known that according to a technique called as a radio-frequency knockout method, the reproducibility of the imparted dose characteristic is high. Such a high reproducibility of the imparted dose characteristic is described in Taku Inaniwa, et al. "Optimization for Fast-Scanning Irradiation in Particle Therapy", Med. Phys. 34, 3302-3311 (2007). In the case where the reproducibility of the imparted dose characteristic is high, even without measurement of the excessive dose value, using the excessive dose value estimated beforehand, it is possible to increase the number of rescan times without a risk of increasing the excessive dose. In Embodiment 5, description will be made about a radiation method in the case where the reproducibility of the imparted dose characteristic is high.

Figure 11A:
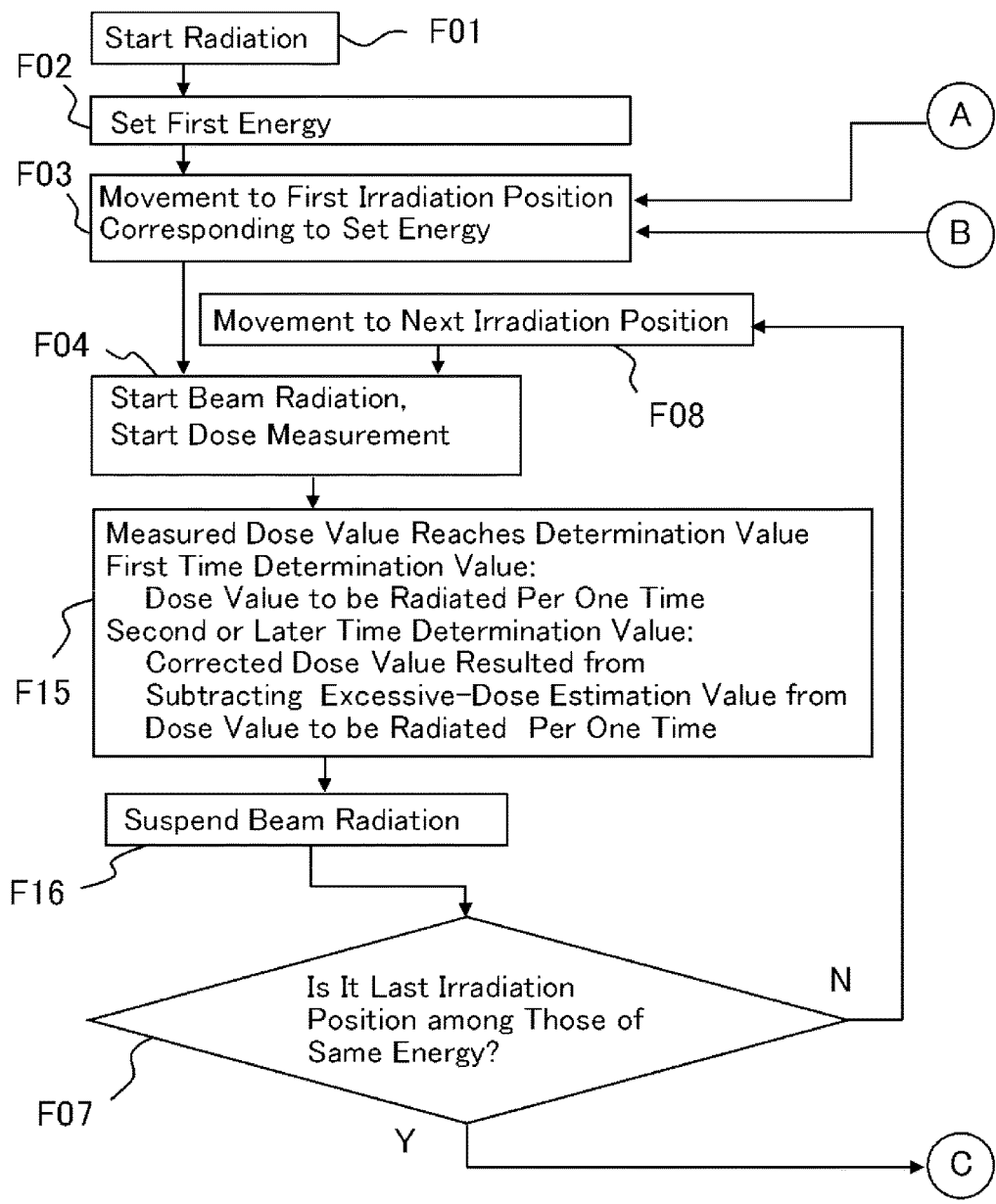
FIG. 11A and FIG. 11B are a set of flowchart showing operations of a particle beam irradiation apparatus according to Embodiment 5 of the invention.
Figure 11B:
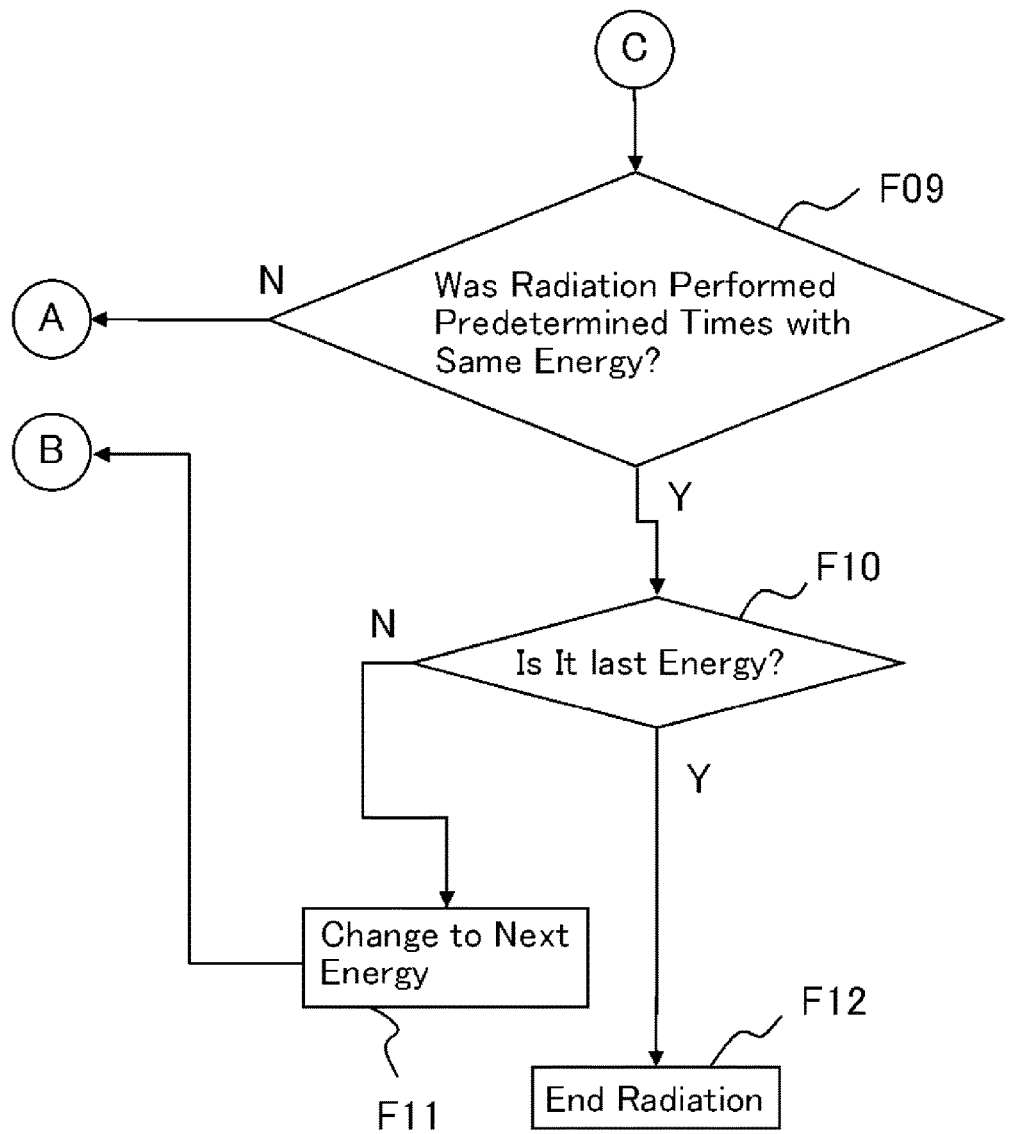

FIG. 11A and FIG. 11B are a set of flowchart showing operations of a particle beam irradiation apparatus according to Embodiment 5 of the invention, and FIG. 12 is a table briefly illustrating an example of information stored in a storage unit according to Embodiment 5 of the invention. The flowchart of FIGS. 11A&11B corresponds to the flowchart of FIGS. 2A&2B in which Step F05 and Step F06 are replaced with Step F15 and Step F16. The example of information 39 in FIG. 12 corresponds to the example of information 33 in FIG. 4 in which excessive doses are replaced with excessive-dose estimation values. Shown in FIG. 12 is an example for the irradiation position number from 1 to m. In "Excessive-Dose Estimation Value" in the storage unit 3, m-pieces of data corresponding to the irradiation position numbers are stored, respectively. For example, at the irradiation position number i, the excessive-dose estimation value ee(i) is stored. The memory regions in which stored is m-number of excessive-dose estimation values are excessive-dose estimation value storing regions.

Operations of the particle beam irradiation apparatus according to Embodiment 5 other than those in the flow in FIGS. 2A&2B will be described. In the case of the first time of radiation to a given irradiation position 12, in Step F15, like in FIGS. 2A&2B, when the value of the measured dose (measured dose value) reaches the value of a divisional target dose (divisional target dose value) that is the value of a target dose per one time (target dose value) and is stored in the storage unit 3, the flow moves to Step F16. In Step F16, the controller 4 issues an instruction for interruption to the particle beam generation-transportation system 1, so that the particle beam generation-transportation system 1 interrupts the particle beam 10.

In the case of the second or later time of radiation to a given irradiation position 12, in Step F15, when the measured dose value reaches the value (corrected dose value) that is smaller just by the excessive-dose estimation value than the target dose value per one time (divisional target dose value) stored in the storage unit 3, the controller 4 issues an instruction for interruption to the particle beam generation-transportation system 1 in Step F16, so that the particle beam generation-transportation system 1 interrupts the particle beam 10.

In the case of the second or later time of radiation to a given irradiation position 12, the particle beam irradiation apparatus 50 of Embodiment 5 regards the corrected dose value that is the value resulted from subtracting the excessive-dose estimation value from the divisional target dose value, as the determination value of the radiation dose. Thus, even without measurement of the excessive dose value, it is possible in the spot scanning method to significantly reduce the total amount of plural times of the excessive doses due to delay of beam interruption. Further, even without measurement of the excessive dose value, the particle beam irradiation apparatus 50 of Embodiment 5 can increase the number of rescan times without a risk of increasing the excessive dose and thus, it is possible to perform radiation with radiation-dose accuracy that is higher than that in the conventional case.

Note that the example of information recorded in the storage unit 3 may instead be another example of information 40 as shown in FIG. 13. FIG. 13 is a table briefly illustrating said another example of information stored in the storage unit according to Embodiment 5 of the invention. In the example of information 40 of FIG. 13, the divisional target dose d(i) and the excessive-dose estimation value ee (i) are not both stored individually, and the corrected dose value dd(i) resulted from subtracting the excessive-dose estimation value ee (i) from the divisional target dose d(i) beforehand is stored.

The memory regions in which stored is m-number of corrected dose values are corrected-dose storing regions.

It should be noted that unlimited combination of the respective embodiments, any modification in the embodiments and any omission in the embodiments may be made appropriately in the present invention without departing from the scope of the invention.

DESCRIPTION OF REFERENCE NUMERALS AND SIGNS

1: particle beam generation-transportation system, 2: scanning device, 3: storage unit, 4: controller, 5: dose monitor, 6: first monitor part, 7: second monitor part, 10: particle beam, 11: irradiation target, 12: irradiation position, 14: excessive dose, 50: particle beam irradiation apparatus.

The invention claimed is:

1. A particle beam irradiation apparatus which comprises: a particle beam generation-transportation system that performs transportation and interruption of an accelerated particle beam; a scanning device that deflects the particle beam transported from the particle beam generation-transportation system in two directions perpendicular to a traveling direction of the beam, to thereby move from one to another of irradiation positions at which an irradiation target is irradiated; a controller that controls the particle beam generation-transportation system and the scanning device; and a dose monitor that measures a dose of the particle beam; wherein the particle beam is radiated plural times to each said irradiation position, and the particle beam is interrupted at the time the irradiation position is being moved;

said particle beam irradiation apparatus including a storage unit in which positional information of the irradiation position and a divisional target dose that is a dose radiated per one time to the irradiation position, are to be stored;

wherein the dose monitor, when the measured dose reaches a value of the divisional target dose, measures an excessive dose radiated from when reaching to that value until radiation of the particle beam is interrupted;

wherein, at a first time of radiation to each said irradiation position, the controller controls the particle beam generation-transportation system and the scanning device to repeat, for up to a last said irradiation position at a same depth in the irradiation target, an operation in which, when the measured dose with respect to one said irradiation position measured by the dose monitor reaches the value of the divisional target dose, the particle beam generation-transportation system interrupts radiation of the particle beam and the scanning device performs deflection control corresponding to a next said irradiation position and thereafter, the particle beam generation-transportation system restarts radiation of the particle beam; and wherein, at a second or later time of radiation to each said irradiation position, the controller controls the particle beam generation-transportation system and the scanning device to repeat just a predetermined number of times, for every said irradiation position at a same depth in the irradiation target, an operation in which, when the measured dose with respect to one said irradiation position measured by the dose monitor reaches a corrected dose value resulted from subtracting a value of the excessive dose at a previous time at that irradiation position from the value of the divisional target dose, the particle beam generation-transportation system interrupts radiation of the particle beam and the scanning device performs deflection control corresponding to a next said irradiation position and thereafter, the particle beam generation-transportation system restarts radiation of the particle beam.

2. The particle beam irradiation apparatus of claim 1, wherein the storage unit includes, for each irradiation position number corresponding to the irradiation position, a divisional target-dose storing region in which the value of the divisional target dose is stored, and an excessive-dose storing region in which the value of the excessive dose is stored;

wherein, in the excessive-dose storing region for each said irradiation position number, at every time the excessive dose is measured, the value of that excessive dose is stored correspondingly to the irradiation position number concerned; and wherein the corrected dose value is a value that is resulted from subtracting the value stored in the excessive-dose storing region of the concerned irradiation position number, from the value stored in the divisional target-dose storing region of the concerned irradiation position number.

3. The particle beam irradiation apparatus of claim 1, wherein the storage unit includes, for each irradiation position number and each irradiation order that are corresponding to the irradiation position, a divisional target-dose storing region in which the value of the divisional target dose is stored, wherein, at every time the excessive dose is measured, in the divisional target-dose storing region that is corresponding to the irradiation position number at which said excessive dose has been measured and that is to be used next time, a value is stored as the corrected dose value, that is resulted from subtracting the value of said excessive dose from the value of the divisional target dose having been stored in that region; and wherein, at the second or later time of radiation to each said irradiation position, the controller regards the corrected dose value stored in the divisional target-dose storing region corresponding to the irradiation position number and the irradiation order concerned, as a determination value for starting to measure the excessive dose.

4. The particle beam irradiation apparatus of claim 1, wherein the storage unit includes, for each irradiation position number corresponding to the irradiation position, a divisional target-dose storing region in which the value of the divisional target dose is stored, and a determination-value storing region in which a determination value for starting to measure the excessive dose next time is stored;

wherein, in the determination-value storing region for each irradiation position number, at every time the excessive dose is measured, a value is stored as the corrected dose value, that is resulted from subtracting the value of said excessive dose from the value of the divisional target dose corresponding to the irradiation position number concerned; and wherein, at the second or later time of radiation to each said irradiation position, the controller regards the corrected dose value stored in the determination-value storing region corresponding to the concerned irradiation position number, as the determination value for starting to measure the excessive dose.

5. The particle beam irradiation apparatus of claim 1, wherein the dose monitor is provided with a first monitor part and a second monitor part;

wherein the first monitor part measures a dose until it reaches a determination value for starting to measure the excessive dose; and wherein the second monitor part measures a dose after the dose measured by the first monitor part reaches the determination value.

6. A particle beam irradiation apparatus which comprises: a particle beam generation-transportation system that performs transportation and interruption of an accelerated particle beam; a scanning device that deflects the particle beam transported from the particle beam generation-transportation system in two directions perpendicular to a traveling direction of the beam, to thereby move from one to another of irradiation positions at which an irradiation target is irradiated; a controller that controls the particle beam generation-transportation system and the scanning device; and a dose monitor that measures a dose of the particle beam; wherein the particle beam is radiated plural times to each said irradiation position, and the particle beam is interrupted at the time the irradiation position is being moved;

said particle beam irradiation apparatus including a storage unit in which positional information of the irradiation position; a divisional target dose that is a dose radiated per one time to the irradiation position; and an excessive-dose estimation value by which estimated is a dose radiated from when an instruction for interrupting radiation to the irradiation position is issued until the radiation is actually interrupted; are to be stored;

wherein, at a first time of radiation to each said irradiation position, the controller controls the particle beam generation-transportation system and the scanning device to repeat, for up to a last said irradiation position at a same depth in the irradiation target, an operation in which, when the measured dose with respect to one said irradiation position measured by the dose monitor reaches the value of divisional target dose, the particle beam generation-transportation system interrupts radiation of the particle beam and the scanning device performs deflection control corresponding to a next said irradiation position and thereafter, the particle beam generation-transportation system restarts radiation of the particle beam; and wherein, at a second or later time of radiation to each said irradiation position, the controller controls the particle beam generation-transportation system and the scanning device to repeat just a predetermined number of times, for every said irradiation position at a same depth in the irradiation target, an operation in which, when the measured dose with respect to one said irradiation position measured by the dose monitor reaches a corrected dose value resulted from subtracting the excessive-dose estimation value for that irradiation position from the value of the divisional target dose, the particle beam generation-transportation system interrupts radiation of the particle beam and the scanning device performs deflection control corresponding to a next said irradiation position and thereafter, the particle beam generation-transportation system restarts radiation of the particle beam.

7. The particle beam irradiation apparatus of claim 6, wherein the storage unit includes, for each irradiation position number corresponding to the irradiation position, a divisional target-dose storing region in which the value of the divisional target dose is stored, and an excessive-dose estimation-value storing region in which the excessive-dose estimation value is stored.

8. The particle beam irradiation apparatus of claim 6, wherein the storage unit includes, for each irradiation position number corresponding to the irradiation position, a divisional target-dose storing region in which the value of the divisional target dose is stored, and a corrected dose value storing region in which the corrected dose value is stored.

9. The particle beam irradiation apparatus of claim 2, wherein the dose monitor is provided with a first monitor part and a second monitor part;

wherein the first monitor part measures a dose until it reaches a determination value for starting to measure the excessive dose; and wherein the second monitor part measures a dose after the dose measured by the first monitor part reaches the determination value.

10. The particle beam irradiation apparatus of claim 3, wherein the dose monitor is provided with a first monitor part and a second monitor part;

wherein the first monitor part measures a dose until it reaches a determination value for starting to measure the excessive dose; and wherein the second monitor part measures a dose after the dose measured by the first monitor part reaches the determination value.

11. The particle beam irradiation apparatus of claim 4, wherein the dose monitor is provided with a first monitor part and a second monitor part;
   wherein the first monitor part measures a dose until it reaches a determination value for starting to measure the excessive dose; and
   wherein the second monitor part measures a dose after the dose measured by the first monitor part reaches the determination value.

\* \* \* \* \*